(12) United States Patent
Chen et al.

(10) Patent No.: US 12,128,143 B2
(45) Date of Patent: Oct. 29, 2024

(54) DISCHARGING MECHANISM OF A MEDICAL WASTE STERILIZATION PROCESSING APPARATUS

(71) Applicant: ZHEJIANG WEIDUN ENVIRONMENTAL TECHNOLOGY CO., LTD., Hangzhou (CN)

(72) Inventors: Yiming Chen, Hangzhou (CN); Weixing Chen, Hangzhou (CN); Junfeng Liu, Hangzhou (CN); Guanzhong Huang, Hangzhou (CN)

(73) Assignee: ZHEJIANG WEIDUN ENVIRONMENTAL TECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 18/671,623

(22) Filed: May 22, 2024

(65) Prior Publication Data
US 2024/0307582 A1 Sep. 19, 2024

Related U.S. Application Data

(63) Continuation of application No. PCT/CN2022/142239, filed on Dec. 27, 2022.

(30) Foreign Application Priority Data

Nov. 23, 2021 (CN) .......................... 202111393609.6

(51) Int. Cl.
*A61L 11/00* (2006.01)
*A61L 2/20* (2006.01)
(Continued)

(52) U.S. Cl.
CPC ................. *A61L 11/00* (2013.01); *A61L 2/20* (2013.01); *A61L 2/24* (2013.01); *A61L 2/26* (2013.01);
(Continued)

(58) Field of Classification Search
None
See application file for complete search history.

(56) References Cited

FOREIGN PATENT DOCUMENTS

CN 200987791 Y * 12/2007

OTHER PUBLICATIONS

Jin, D. CN200987791Y—translated document (Year: 2007).*

* cited by examiner

*Primary Examiner* — Jelitza M Perez
(74) *Attorney, Agent, or Firm* — Westbridge IP LLC (57) ABSTRACT

A discharging mechanism of a medical waste sterilization processing apparatus includes a central processing module, a waste processing module, a sterilization module, a monitoring module, a protection module, and a discharge module. The waste processing module and the sterilization module are communicatively connected to the central processing module, the sterilization module is connected to the waste processing module for sterilizing the waste processing module; the monitoring module is provided at the connection of the sterilization module and the waste processing module and is communicatively connected to the central processing module; the protection module is provided in the waste processing module and communicating with the central processing module; the discharge module is connected to the waste processing module and the protection module for discharging processed medical waste. The apparatus has an emergency treatment function to cope with a leakage situation, thereby improving its safety coefficient.

6 Claims, 8 Drawing Sheets

(51) Int. Cl.
　　*A61L 2/24*　　　(2006.01)
　　*A61L 2/26*　　　(2006.01)
　　*B09B 3/70*　　　(2022.01)
　　*B09B 101/65*　　(2022.01)
(52) U.S. Cl.
　　CPC ............ *B09B 3/70* (2022.01); *A61L 2202/14*
　　　　　(2013.01); *B09B 2101/65* (2022.01)

DISCHARGING MECHANISM OF A MEDICAL WASTE STERILIZATION PROCESSING APPARATUS

CROSS-REFERENCE TO RELATED APPLICATIONS

The present application is a continuation of International Application No. PCT/CN2022/142239, filed on Dec. 27, 2022, which claims priority to Chinese Patent Application No. 202111393609.6, filed on Nov. 23, 2021. The disclosures of the above-mentioned applications are incorporated herein by reference in their entireties.

TECHNICAL FIELD

The present application relates to the technical field of medical waste treatment, specifically to a discharging mechanism of a medical waste sterilization treatment equipment.

BACKGROUND

Medical waste is waste generated in the process of patient diagnosis, treatment, nursing, and other activities. Medical waste may contain a large number of pathogenic microorganisms and harmful chemicals, and may even contain radioactive and damaging substances, so medical waste is an important risk factor for disease transmission or related public health problems.

The volume of medical waste treatment is increasing, while existing medical waste processing apparatus does not have an automatic discharging mechanism, and thus cannot be automatically discharged, thus limiting the efficiency of medical treatment. In addition, the exhaust gas of medical treatment often contains toxic substances, which will spill out from the discharge opening when the equipment leaks, so the discharging mechanism of medical treatment apparatus needs to have certain protective functions.

SUMMARY

The purpose of the present application is to provide a medical waste sterilization treatment apparatus discharging mechanism, to achieve automatic discharge of medical waste, and at the same time have emergency treatment function when the apparatus has a leak, thus improve the safety coefficient of the equipment.

The application proposes a technical solution as follows.

A discharging mechanism of a medical waste sterilization processing apparatus comprises: a central processing module, a waste processing module, a sterilization module, a monitoring module, a protection module, and a discharge module; wherein the waste processing module and the sterilization module are both communicatively connected to the central processing module, and the sterilization module is connected to the waste processing module for sterilizing the waste processing module; the monitoring module is arranged at a connection between the sterilization module and the waste processing module, and is communicatively connected to the central processing module; the protection module is arranged inside the waste processing module and is communicatively connected to the central processing module; the discharge module is connected to the waste processing module and the protection module for discharging the processed medical waste.

Further, the waste processing module comprises a fixed part, the fixed part having a containing cavity, the containing cavity having a processing cylinder rotatably set inside the containing cavity, and the processing cylinder is provided with an intermittent discharge section used for discharging the treated medical waste from the processing cylinder after treatment has been completed.

Further, the fixed part is provided with a discharge opening and the discharge module is provided at the discharge opening.

Further, the discharge module comprises a receiving section, the receiving section is provided in the containing cavity and is located between the discharge opening and the intermittent discharge section, the receiving section is provided with a first electromagnetic retractable plate on both sides, the first electromagnetic retractable plate is used to connect an outlet of the intermittent discharge section to the discharge opening.

Further, the protection module comprises a closing assembly, arranged inside the containing cavity and positioned near the discharge opening, and the closing assembly is located on a side of the receiving section close to the discharge opening and is used to seal the discharge opening.

Further, the closure assembly comprises an electromagnetic drive assembly, an output end of the electromagnetic drive assembly is provided with a second electromagnetic retractable plate, and the second electromagnetic retractable plate is located between the discharge opening and the receiving section.

Further, the second electromagnetic retractable plate has an arc-shaped surface on the side facing the discharge opening and is fitted to the inner side wall of the containing cavity.

Preferably, the discharge module further includes: a discharge hopper, arranged obliquely downward in a vertical direction at the discharge opening; a transfer assembly, hinged to a side wall of the discharge opening, which is used for transferring waste from the receiving section to the discharge hopper; a driving assembly which is used for driving the transfer assembly in motion, arranged outside the fixed part, with its output end connected to the transfer assembly.

Further, the transfer assembly comprises two first hinged plates, with one end of each first hinged plate rotatably arranged on two side walls of the discharge opening via a first hinge shaft, and a push plate is fixedly arranged between the two first hinged plates; the end of each first hinged plate far from the first hinge shaft is provided with a second hinged plate, with the second hinged plate hinged to the first hinged plate via a second hinge shaft, and the other end of the second hinged plate is fixedly connected to the output end of the driving assembly.

Further, the driving assembly comprises a driving motor fixedly provided on the outer side of the fixed part, and an output end of the driving motor is fixedly provided with a third hinge shaft, and the other end of the third hinge shaft is hinged to a third hinged plate, with the other end of the third hinged plate connected to the second hinged plate via a fourth hinge shaft.

The present application provides herein an improved discharge mechanism for medical waste sterilization processing apparatus, has the following improvements and advantages compared to existing technology.

By setting up the discharge module, this equipment can achieve automatic discharge and collection of medical waste. Furthermore, the discharge module is in communication with the protective module. In the event of equipment leakage, the discharge opening of the discharge module can be automatically sealed, thus preventing exhaust gas from escaping through the discharge opening and improving the safety of the equipment.

BRIEF DESCRIPTION OF THE DRAWINGS

The present application is further explained in the following with the attached drawings and examples.

DETAILED DESCRIPTION OF THE EMBODIMENTS

The core of the present application is to provide a discharging mechanism for medical waste sterilization processing apparatus.

The present application will be described in detail hereinafter in conjunction with the accompanying FIGS. 1 to 9 to provide a clear and complete description of the technical solutions in the embodiments of the present application, and it is clear that the described embodiments are only a part of the embodiments of the present application, and not all of them. Based on the embodiments in the present application, all other embodiments obtained by a person of ordinary skill in the art without making creative labor fall within the scope of protection of the present application.

It should be noted that the descriptions such as "first" and "second" used in the embodiments of the present application are used for descriptive purposes only and should not be understood as indicating or implicitly indicating the number of technical features limited, thus, the embodiments of the present specification are limited to the "first" and "second" features in each embodiment of the specification may indicate the inclusion of at least one of the defined technical features.

The technical solutions between the embodiments of the application described in this specification may be combined with each other, but only on the basis that they can be realized by a person of ordinary skill in the art, and when the combination of technical solutions appears to be contradictory or cannot be realized, the combination of technical solutions shall be deemed not to exist.

As shown in FIGS. 1 to 9, the discharging mechanism of a medical waste sterilization processing apparatus of the present application comprises: a central processing module, a waste processing module, a sterilization module 2, a monitoring module, a protection module 5, and a discharge module 6.

The waste processing module and the sterilization module 2 are both communicatively connected to the central processing module, and the sterilization module 2 is connected to the waste processing module for sterilizing the waste processing module.

The monitoring module is arranged at a connection between the sterilization module and the waste processing module, and is communicatively connected to the central processing module.

The protection module 5 is arranged inside the waste processing module and is communicatively connected to the central processing module.

The discharge module 6 is connected to the waste processing module and the protection module 5 for discharging the processed medical waste.

In the present application, the monitoring module includes sensors for detecting leaks at the connections. When the monitoring module detects a leak at any of the connections between the sterilization module 3 and the waste processing module, it transmits a signal to the central processing module. The central processing module then sends a command to the protection module 5. Upon receiving the command, the protection module 5 activates, isolating the waste processing module to prevent further leakage of harmful gases. Simultaneously, the discharge module 6 stops operating, and the protection module seals the discharge channel to prevent exhaust gases from being emitted through the discharge module 6, thereby enhancing the safety of the application.

Furthermore, the discharge mechanism also includes a control panel and a facial recognition module. The facial recognition module is used to determine whether the operator is wearing a protective mask. Only when the operator is wearing a protective mask can they press the unlock button on the control panel to deactivate the protection module, allowing for the maintenance of the entire device. This prevents accidental deactivation of the discharge mechanism by the operator, thereby ensuring the operator's personal safety.

In one embodiment of the present application, the waste processing module includes a fixed part 21, which has a containing cavity. A processing cylinder, equipped with processing components for treating medical waste, is rotatably set inside the containing cavity. The opening of the processing cylinder 23 is located inside the containing cavity, and a cover 22 is hinged at the opening of the containing cavity. The processing cylinder is equipped with an intermittent discharge section, which is used to discharge the treated medical waste from the processing cylinder 23.

Before treating the medical waste, the cover 22 is opened, and the medical waste to be treated is placed into the processing cylinder for treatment. The cover 22 ensures that the processing cylinder 23 is in a closed space, thereby preventing the generated exhaust gases from escaping through the opening. It should be noted that the processing components for treating medical waste are existing technologies and are not elaborated here.

Furthermore, when the medical waste in the processing cylinder 23 has been treated, the intermittent discharge section can discharge the medical waste from the processing cylinder 23, thereby achieving continuous and uninterrupted treatment of medical waste. It should be noted that the intermittent discharge section is any existing technology for intermittently transferring objects out of the processing cylinder, and thus is not elaborated here.

In one embodiment of the present application, the fixed part 21 is provided with a discharge opening, the discharge module 6 is provided at the discharge opening, and by providing the discharge opening and by arranging the discharge module 6 at the discharge opening, it is thus convenient to discharge the medical waste.

In an embodiment of the present application, the discharge module 6 comprises a receiving section 64, the receiving section 64 is provided in the containing cavity and is located between the discharge opening and the intermittent discharge section, the receiving section 64 is provided with a first electromagnetic retractable plate on both sides, the first electromagnetic retractable plate is used to connect the outlet of the intermittent discharge section with the discharge opening.

By providing the receiving section 64 and the electromagnetic retractable plate on the receiving section 64, the discharge module 6 stops working when the exhaust gas leaks from the medical waste processing apparatus, and the first electromagnetic retractable plate retracts, thus enabling the protection module 5 to seal the discharge opening, so that the exhaust gas will not leak from the discharge opening, thus improving the safety of the present application.

In one embodiment of the present application, the processing cylinder 23 is coaxially aligned with the fixed part 21 and has an installation gap between it and the containing cavity. The side wall of the fixed part 21 is provided with mounting holes, and the fixed part 21 is connected to the sterilization module 3 via connecting components 4. The connecting end of the connecting component 4 with the fixed part 21 is located within the mounting hole. Multiple communication holes are uniformly provided on the side wall of the processing cylinder 23 at positions for air circulation. It should be noted that an isolation plate is also installed in the installation gap between the processing cylinder 23 and the fixed part 21, so that the air circulation of the sterilization module does not directly communicate with the discharge module 6, thereby preventing exhaust gases from being emitted through the discharge module 6 when the equipment is not leaking. In one embodiment of the present application, the protection module comprises a closure assembly 58, which is provided within the containing cavity and located at a position close to the discharge opening. The closure assembly 58 is located on the side of the receiving section 64 near the discharge opening, and it is used to close the discharge opening.

Further, the closure assembly 58 includes an electromagnetic drive assembly 581, at the output end of which a second electromagnetic retractable plate 582 is provided; the second electromagnetic retractable plate 582 is located between the discharge opening and the receiving section 64.

When the medical waste processing apparatus leaks, the drive assembly 581 drives the second electromagnetic retractable plate 582 to move, thereby causing the second electromagnetic retractable plate 582 to seal the discharge opening, thereby preventing the waste gas from overflowing from the discharge opening and thus improving the safety of the present application.

Further, the second electromagnetic retractable plate 582 has an arc-shaped surface on the side facing the discharge opening and fits against the inner side wall of the containing cavity, thereby enabling the second electromagnetic retractable plate 582 to better seal the discharge opening and improve the sealing performance during sealing.

In an embodiment of the present application, the discharge module 6 further includes: a discharge hopper 61 provided at the discharge opening, the hopper 61 is provided diagonally downward along a vertical direction; a transfer assembly 62, hinged on the side wall of the discharge opening for transferring waste from the receiving section 64 to the hopper 61; a drive assembly 63, provided outside of the fixed section 21, the drive assembly 63 is provided outside fixed part 21, the output end of the drive assembly 63 is connected to the transfer assembly 62 for driving the movement of the transfer assembly 62.

The transfer assembly 62 includes two first two first hinge plates 621, each pivotally mounted at one end on the side walls of the discharge port via a first hinge axis 622. A push plate 623 is fixedly positioned between the two first hinge plates 621. At the end away from the first hinge axis 622, each first hinge plate 621 is pivotally connected to a second hinge plate 624 via a second hinge axis, and the other end of the second hinge plate 624 is fixedly connected to the output end of the drive component 63.

The drive assembly 63 includes a drive motor 631, fixedly positioned on the outer side of the fixed part 21, with its output end fixedly connected to a third hinge axis 632. Another hinge of the third hinge axis 632 is connected to a third hinge plate 633, and the other end of the third hinge plate 633 is connected to the second hinge plate 624 via a fourth hinge axis 634.

During the discharging process, the drive motor 631 drives the movement of the third hinge axis 632, which in turn drives the movement of the third hinge plate 633, causing the second hinge plate 624 to move via the fourth hinge axis 634. The movement of the second hinge plate 624 drives the second hinge axis, thus moving the first hinge plate 621. As the other end of the first hinge plate 621 is pivotally mounted on the side wall of the discharge port via the first hinge axis 622, the overall movement trajectory of the push plate 623 is elliptical. This enables the push plate 623 to scrape the medical waste on the receiving part 64 into the discharge chute 61 during its movement, thereby discharging it outside the fixed part 21 for collection, achieving automatic discharge of medical waste.

In one embodiment of the present application, due to the coaxial arrangement of the processing cylinder 23 with the fixed part 21 and the installation gap between it and the containing cavity, convenient installation of other components of the protection module 5 is facilitated. Moreover, communication holes are provided on the side wall of the processing cylinder 23, allowing the sterilizing gas from the sterilization module 3 to be introduced into the containing cavity via the connecting component 4 and then into the processing cylinder 23 for sterilization. The sterilization module 3 and the processing module 2 are connected by the connecting component 4 to form a closed loop for circulation, enabling collection and treatment of waste gases generated during the medical waste processing and recycling of sterilizing gases, thereby improving the practicality of the application. It should be noted that the specific technical solutions for waste gas collection and treatment in the sterilization module 3, as well as the recycling of sterilizing gases, are all part of the prior art and are not further elaborated here.

In one embodiment of the present application, the connecting component 4 includes an intake connection pipe 41 and an exhaust connection pipe 42, which are respectively located on both sides of the fixed part 21 and arranged alternately along the height direction.

By configuring the intake connection pipe 41 and the exhaust connection pipe 42, gas circulation is achieved. The intake connection pipe 41 and the exhaust connection pipe 42 are respectively arranged on both sides of the fixed part 21 and are staggered in the height direction. More specifically, the intake connection pipe 41 is positioned on the side of the fixed part 21 near the sterilization module 3, located at an end near the opening of the fixed part 21, while the exhaust connection pipe 42 is positioned on the side of the fixed part 21 away from the sterilization module and located at the end away from the opening of the fixed part 21. This makes the length of the intake connection pipe 41 shorter than that of the exhaust connection pipe 42, allowing the sterilizing gas to enter the processing module 2 from the sterilization module 3 more quickly, while the exhaust gas can enter the sterilization module more slowly for subsequent treatment. Further technical refinement can involve installing filter adsorption components inside the exhaust connection pipe to ensure more comprehensive and thorough filtration of the exhaust gas, thereby enhancing the utility of the application.

At the same time, the intake connection pipe 41 is positioned at the end near the opening of the fixed part 21, which is spatially closer to the human face. This means that in the event of a leak, the concentration of harmful gases near the human face will be lower than in other parts, reducing the risk of workers accidentally inhaling harmful gases and thus improving the practicality of the application.

Moreover, the staggered arrangement of the intake connection pipe 41 and the exhaust connection pipe 42 in the height direction ensures more thorough sterilization of the gas in the processing module 2, thereby enhancing the sterilization effect.

In one embodiment of the present application, the protection module 5 is arranged inside the containing cavity and includes a sealing assembly for sealing the connecting component 4 and a locking component for locking the cover plate. The sealing assembly is used to block the intake connection pipe 41 and the exhaust connection pipe 42, ensuring that the processing module 2 is entirely isolated and preventing the spread of toxic gases such as exhaust gases to the outside. The locking component ensures that the cover 22 is in a locked state, preventing the cover 22 from being opened accidentally by workers and thus preventing operational errors.

In one embodiment of the present application, the sealing assembly includes a first connecting pipe 51, positioned on one side of the connecting component 4 outside and fixedly connected to the inner side wall of the containing cavity via a connecting part 52. On the side inside the connecting component 4, the first connecting pipe 51 is coaxially and fixedly sleeved with a blocking element 55, which is in communication with the first connecting pipe 51; a second connecting pipe 53 is in communication with the first connecting pipe 51, with its input end connected to an external gas source.

The blocking element 55 is an annular airbag with an initial outer diameter smaller than the inner diameter of the connecting component 4.

When the protection module 5 starts operating, the external gas source activates, introducing gas through the second connecting pipe 53, then into the first connecting pipe 51, and finally into the blocking element 55, causing it to expand and completely seal the inner wall of the connecting component 4, thereby preventing further leakage of exhaust gas.

In one embodiment of the present application, the first connecting pipe 51 is connected to the second connecting pipe 53 via a third connecting pipe 54. By providing the third connecting pipe 54, the number of sealing assemblies can be unlimited, and multiple branches can be set on the second connecting pipe 53 to supply gas to each first connecting pipe 51. It should be noted that multiple circulation loops for connections, such as steam circulation loops, can be set between the sterilization module 3 and the processing module 2 for the treatment of medical waste, allowing the application to block the connection points of each loop, thereby enhancing the utility of the application.

In one embodiment of the present application, the locking component includes a driving member 56, which is connected to the sealing assembly. The driving member 56 is fixedly mounted on a connecting base 212 on the inner wall of the containing cavity. An electromagnetic plate 57 is slidably arranged on the driving member 56. The opening of the containing cavity is provided with an opening 211, and a catching plate 221 is fixedly arranged on the side of the cover 22 near the opening 211. When the cover 22 is closed, the catching plate 221 is located within the opening 211.

During operation, the driving member 56 moves the electromagnetic plate 57 towards the catching plate 221. When the electromagnetic plate 57 comes into contact with the catching plate 221, the electromagnetic plate 57 is energized, forming an electromagnet, thereby attracting the catching plate 221 and locking the cover 22. It should be noted that the driving member 56 includes an air duct chamber 561 running through it. One end of the air duct chamber 561 is connected to the second connecting pipe 53, and a piston plate 562 is arranged inside the air duct chamber 561 near the side connected to the second connecting pipe 53. A push rod 563 is arranged on the side of the piston plate 562 close to the electromagnetic plate 57, and the other end of the push rod 563 is fixedly connected to the electromagnetic plate 57.

Figure 1:
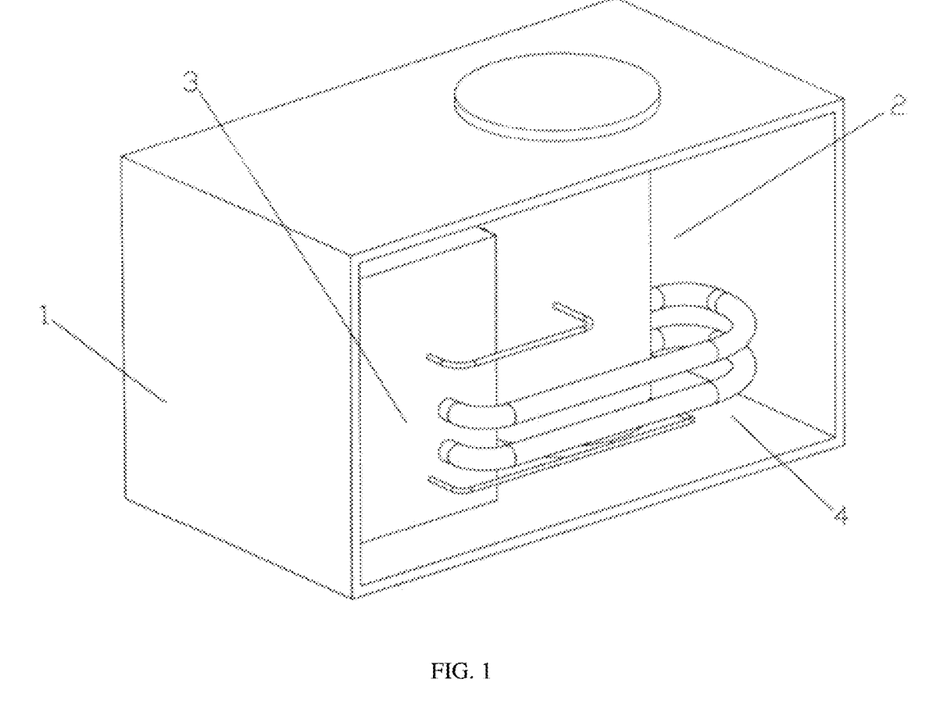
FIG. 1 is a schematic diagram of a first isometric structure of the present application.
Figure 2:
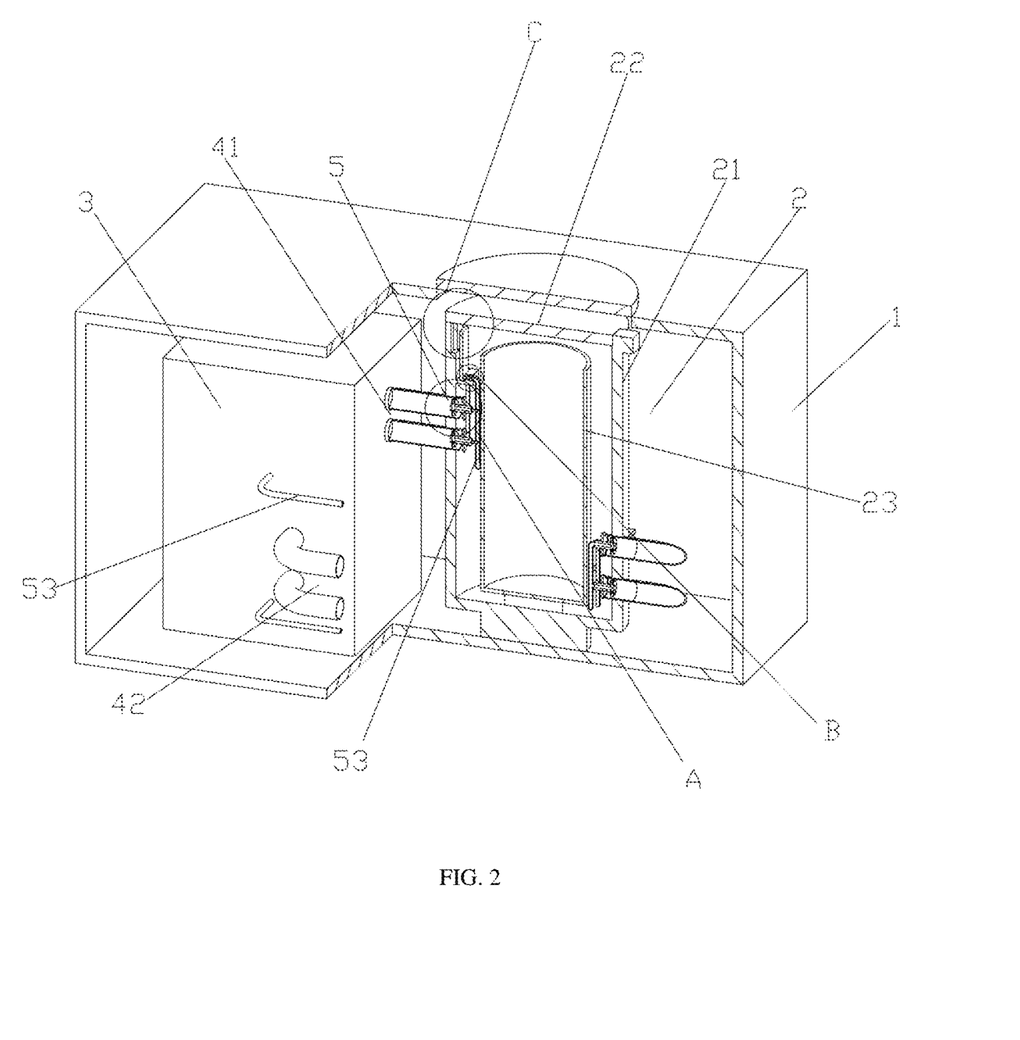
FIG. 2 is a schematic diagram of the first isometric section structure of the present application.
Figure 3:
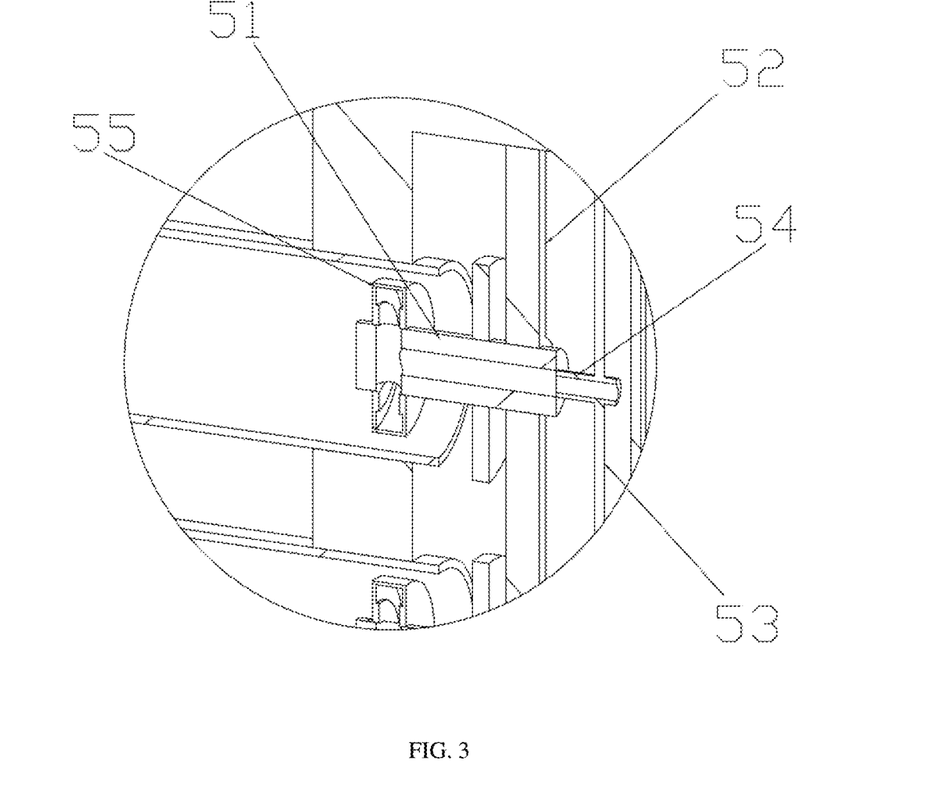
FIG. 3 shows an enlarged view of area A in FIG. 2.
Figure 4:
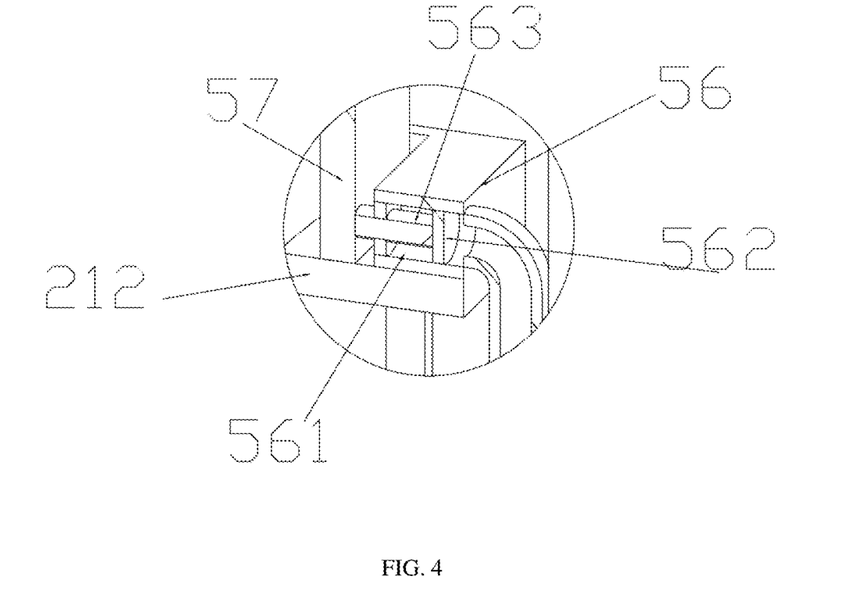
FIG. 4 shows an enlarged view of area B in FIG. 2.
Figure 5:
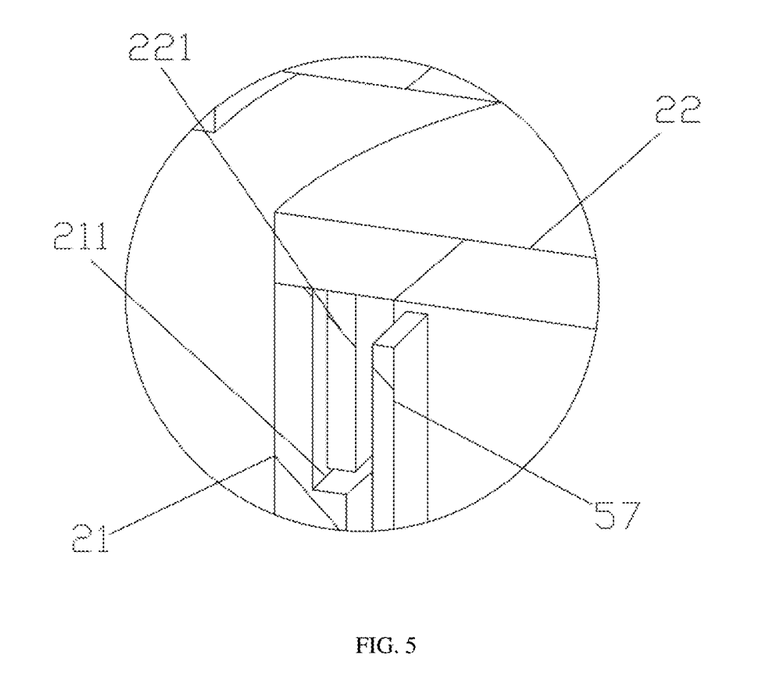
FIG. 5 shows an enlarged view of area C in FIG. 2.
Figure 6:
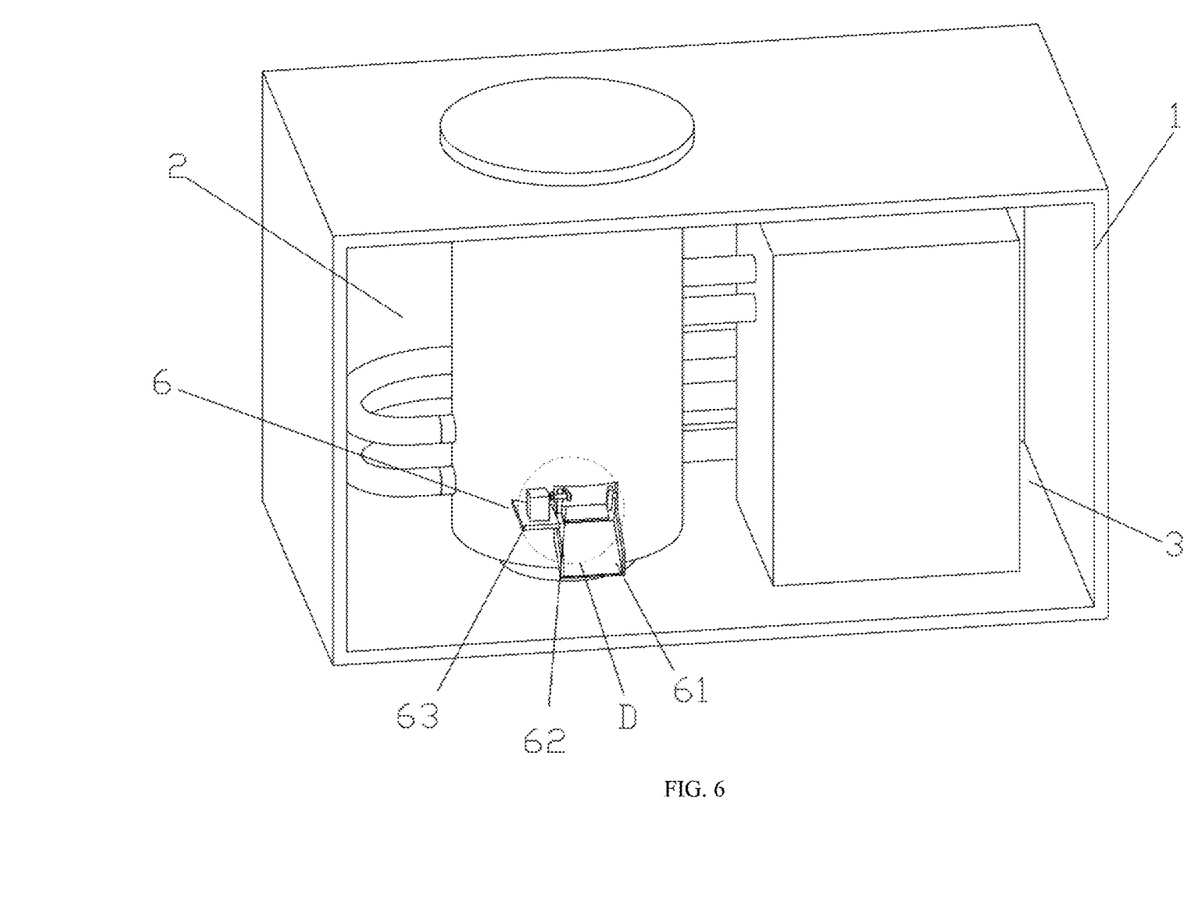
FIG. 6 is a schematic diagram of the second isometric structure of the present application.
Figure 7:
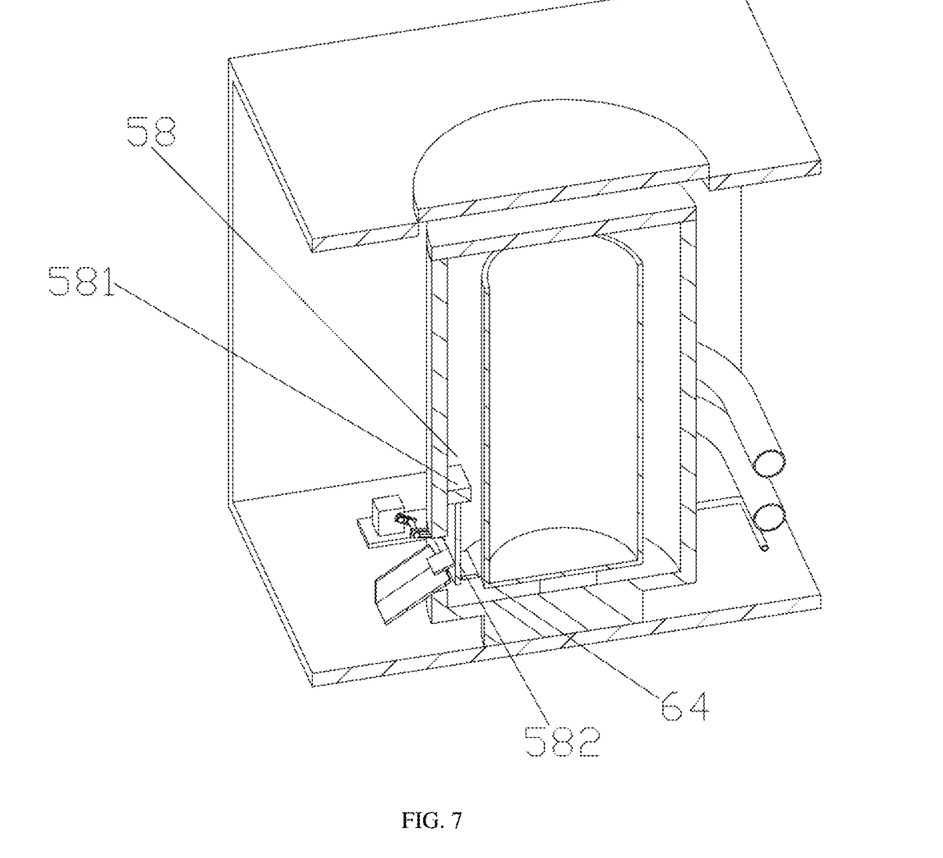
FIG. 7 is a schematic diagram of a second isometric sectional structure of the present application.
Figure 8:
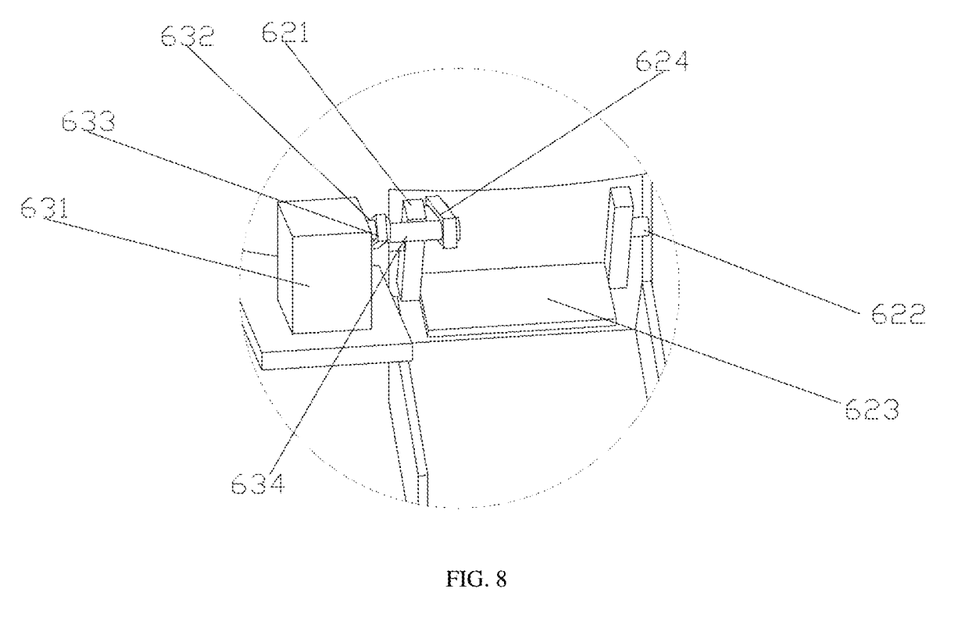
FIG. 8 is an enlarged view of area D in FIG. 6.
Figure 9:
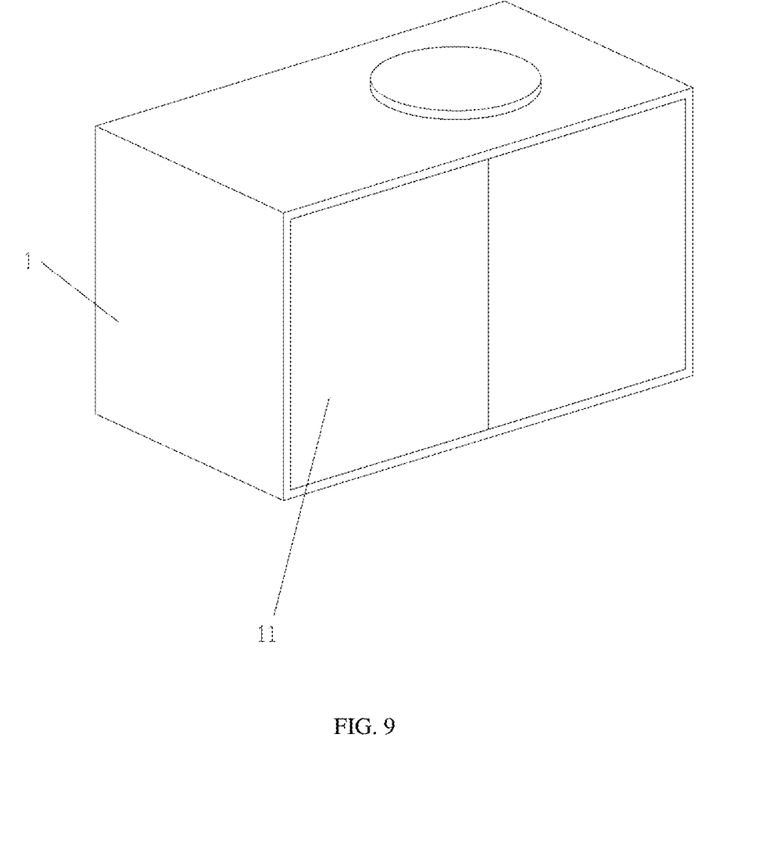
FIG. 9 is a schematic diagram of an isometric structure of the connection structure of the cabinet door in the present application.

In one embodiment of the present application, a cabinet 1 is also included. Both sides of the cabinet 1 are equipped with cabinet doors 11, each fitted with an electronic lock. The electronic locks are in communication with the central processing module. When the monitoring module detects a leak at any connection point between the sterilization module 3 and the waste processing module 2, it sends a signal to the central processing module. The central processing module then sends a command to the electronic locks. Upon receiving the command, the electronic locks lock the cabinet doors 11, preventing the staff from opening them normally. The cabinet doors 11 can only be unlocked through an external facial recognition module and control panel.

The above description is merely a preferred embodiment of the present application and does not limit the scope of its patent protection. Any equivalent structural or process changes made according to the specification and drawings of the present application, or directly or indirectly applied to other related technical fields, are included within the scope of the patent protection of the present application.

What is claimed is:

1. A discharging mechanism of a medical waste sterilization processing apparatus, comprising: a central processing module, a waste processing module, a sterilization module, a monitoring module, a protection module, and a discharge module; wherein
   the waste processing module and the sterilization module are both communicatively connected to the central processing module, and the sterilization module is connected to the waste processing module for sterilizing the waste processing module;
   the monitoring module is arranged at a connection between the sterilization module and the waste processing module, and is communicatively connected to the central processing module;
   the protection module is arranged inside the waste processing module and is communicatively connected to the central processing module;

the discharge module is connected to the waste processing module and the protection module for discharging the processed medical waste;

the waste processing module comprises a fixed part with a containing cavity, within which a processing cylinder is rotatably arranged, and the processing cylinder is provided with an intermittent discharge section for discharging processed medical waste from the processing cylinder; a discharge opening is provided on the fixed part, with the discharge module arranged at the discharge opening;

the discharge module comprises a receiving section, arranged inside the containing cavity and located between the discharge opening and the intermittent discharge section, and both sides of the receiving section are equipped with a first electromagnetic retractable plate to connect an outlet of the intermittent discharge section to the discharge opening; the discharge module further comprises a discharge hopper arranged obliquely downward in a vertical direction at the discharge opening; and the discharge module further comprises a transfer assembly hinged to a side wall of the discharge opening, which is used for transferring waste from the receiving section to the discharge hopper; the discharge module further comprises a driving assembly arranged outside the fixed part, with its output end connected to the transfer assembly, which is used for driving the transfer assembly.

2. The discharging mechanism for the medical waste sterilization processing apparatus according to claim 1, wherein the protection module comprises a closing assembly, arranged inside the containing cavity and positioned near the discharge opening, and the closing assembly is located on a side of the receiving section close to the discharge opening and is used to seal the discharge opening.

3. The discharging mechanism for the medical waste sterilization processing apparatus according to claim 2, wherein the closing assembly comprises an electromagnetic driving assembly, with a second electromagnetic retractable plate at its output end, and the second electromagnetic retractable plate is positioned between the discharge opening and the receiving section.

4. The discharging mechanism for the medical waste sterilization processing apparatus according to claim 3, wherein the second electromagnetic retractable plate has an arc-shaped surface on a side facing the discharge opening and fits closely with an inner side wall of the containing cavity.

5. The discharging mechanism for the medical waste sterilization processing apparatus according to claim 1, wherein the transfer assembly comprises two first hinged plates, with one end of each first hinged plate rotatably arranged on two side walls of the discharge opening via a first hinge shaft, and a push plate is fixedly arranged between the two first hinged plates; an end of each first hinged plate far from the first hinge shaft is provided with a second hinged plate, with the second hinged plate hinged to the first hinged plate via a second hinge shaft, and the other end of the second hinged plate is fixedly connected to the output end of the driving assembly.

6. The discharging mechanism for the medical waste sterilization processing apparatus according to claim 5, wherein the driving assembly comprises a driving motor fixedly arranged on the outer side of the fixed part, and an output end of the driving motor is fixedly provided with a third hinge shaft, and the other end of the third hinge shaft is hinged to a third hinged plate, with the other end of the third hinged plate connected to the second hinged plate via a fourth hinge shaft.

\* \* \* \* \*